(12) United States Patent
Wang et al.

(10) Patent No.: US 11,419,862 B2
(45) Date of Patent: Aug. 23, 2022

(54) QUINOLINE DERIVATIVE FOR TREATMENT OF NASOPHARYNGEAL CARCINOMA

(71) Applicant: CHIA TAI TIANQING PHARMACEUTICAL GROUP CO., LTD., Jiangsu (CN)

(72) Inventors: Shanchun Wang, Jiangsu (CN); Jun Shen, Jiangsu (CN); Xi Han, Jiangsu (CN); Xunqiang Wang, Jiangsu (CN); Shaonan Tang, Jiangsu (CN); Shuqing Cao, Jiangsu (CN); Xiquan Zhang, Jiangsu (CN); Hao Yu, Jiangsu (CN); Maoqiong Pan, Jiangsu (CN); Ping Xu, Jiangsu (CN); Chengqian Wang, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 67 days.

(21) Appl. No.: 16/937,471

(22) Filed: Jul. 23, 2020

(65) Prior Publication Data

US 2020/0352932 A1 Nov. 12, 2020

Related U.S. Application Data

(63) Continuation-in-part of application No. PCT/CN2019/077244, filed on Mar. 7, 2019.

(30) Foreign Application Priority Data

Mar. 14, 2018 (CN) .......................... 201810206825.7
May 23, 2019 (CN) .......................... 201910433564.7

(51) Int. Cl.
*A61K 45/06* (2006.01)
*A61K 31/4709* (2006.01)

(52) U.S. Cl.
CPC .......... *A61K 31/4709* (2013.01); *A61K 45/06* (2013.01)

(58) Field of Classification Search
CPC .......................... A61K 31/4709; A61K 45/06
USPC ........................................................ 514/312
See application file for complete search history.

(56) References Cited

U.S. PATENT DOCUMENTS

2017/0182027 A1* 6/2017 Wang .................. A61K 9/1075
2017/0266188 A1 9/2017 Yan et al.

FOREIGN PATENT DOCUMENTS

| CN | 101809012 | 8/2010 |
| CN | 105311030 | 2/2016 |
| CN | 105311030 A | 2/2016 |
| EP | 3 120 851 | 1/2017 |
| WO | 2008/112407 | 9/2008 |
| WO | WO-2008112407 A1 | 9/2008 |
| WO | 2017/118401 | 7/2017 |
| WO | 2019140937 | 7/2019 |
| WO | 2020/057536 | 3/2020 |

OTHER PUBLICATIONS

Liu et al Journal of Translational Medicine 2013, 11:140 pp. 1-13 (Year: 2013).*
Punagi et al The Open Otorhinolaryngology Journal, 2013, 7, 10-13 (Year: 2013).*
Peng, H., Chen, L., Li, WF. et al. The Cumulative Cisplatin Dose Affects the Long-Term Survival Outcomes of Patients with Nasopharyngeal Carcinoma Receiving Concurrent Chemoradiotherapy. Sci Rep 6, 24332 (2016). (Year: 2016).*
Jain et al., Chin. Clin. Oncol. 2016 5(2):22 1-10 (Year: 2016).*
Mi et al Oral Oncology, 2017, 74, 34-39 (Year: 2017).*
International Search Report and Written Opinion for International Application No. PCT/CN2019/077244, dated Jun. 12, 2019, National Intellectual Property Administration, People's Republic of China, 11 pages (With Translation).
Pend, Q.X. et al., "Apatinib inhibits VEGFR-2 and angiogenesis in an in vivo murine model of nasopharyngeat carcinoma", Oncotarget, vol. 8, No. 32, Aug. 8, 2017, pp. 52813-52822.
Isakoff, M.S., "Osteosarcoma: Current Treatment and a Collaborative Pathway to Success", Journal of Clinical Oncology, 2015, vol. 33(27), pp. 3029-3035.
Bishop, M. et al., "Future directions in the treatment of osteosarcoma", Current Opinion in Pediatrics, 2016, vol. 28 (1), pp. 26-33.
Bovee, J., et al., "Emerging pathways in the development of chondrosarcoma of bone and implications for targeted treatment", Lancet Oncology, 2005, vol. 6(8), pp. 599-607.
Macdonald, I. J. et al., "An update on current and future treatment options for chondrosarcoma", Expert Rev Anticancer Ther., 2019, vol. 19(9), pp. 773-786.
Chi, Y. et al., "Safety and Efficacy of Anlotinib, a Multikinase Angiogenesis Inhibitor, in Patients with Refractory Metastatic Soft-Tissue Sarcoma", American Associate for Cancer Research, 2018, pp. 5233-5238.
Shen, G. et al., "Anlotinib: a novel multi-targeting tyrosine kinase inhibitor in clinical development", J. Hematol. Oncol., 2018, vol. 11(1), pp. 120.
Luetke, A. et al., "Osteosarcoma treatment—where do we stand? A state of the art review", Cancer Treat. Rev., 2014, vol. 40(4), pp. 523-532.
Tian, Z. et al., "Retrospective review of the activity and safety of apatinib and anlotinib in patients with advanced osteosarcoma and soft tissue sarcoma", Ivestigational New Drugs, 2020, vol. 28, pp. 1559-1569.
Gao, T. et al., "Advances in Molecular Targeted Therapy for Soft Tissue Sarcoma", Chinese Journal of Clinical Oncology, 2017, vol. 44(1), pp. 1-8.
Fu, G. et al., "Research progess of vascular endothelial growth factor in osteosarcoma", Chongqing Medical University, 2009, pp. 1180-1182. (English Abstract).
Li, X. et al., "Expression of C-kit receptor and platelet-derived growth factor receptor-α in osteosarcoma and their significance", J. Clin. Exp. Pathol., 2013, vol. 29(8), pp. 868-875. (English Abstract).
Gao, T. et al., "Research progress in molecular targeted therapy of soft tissue sarcoma", Chin J Clin Oncol, 2017, vol. 44(1), pp. 7-13 (English Abstract).
Extended European Search report of International Application No. 19740851.1 dated Sep. 16, 2021.

* cited by examiner

*Primary Examiner* — Yevgeny Valenrod
(74) *Attorney, Agent, or Firm* — Ping Wang; Rimon Law

(57) ABSTRACT

The present invention provides a quinoline derivative for the treatment of nasopharyngeal carcinoma and use thereof in preparation of a pharmaceutical composition for tumor treatment.

22 Claims, No Drawings

QUINOLINE DERIVATIVE FOR TREATMENT OF NASOPHARYNGEAL CARCINOMA

CROSS-REFERENCE TO RELATED APPLICATIONS

This application is a continuation-in-part of International Application No. PCT/CN2019/077244, filed on Mar. 7, 2019, which claims priority to Chinese Patent Application No. 201810206825.7, filed on Mar. 14, 2018; this application also claims priority to Chinese Patent Application No. 201910433564.7, filed on May 23, 2019; all of which are hereby incorporated by reference in their entirety.

TECHNICAL FIELD

The present invention belongs to the technical field of medicine, and specifically relates to use of a quinoline derivative for treating nasopharyngeal carcinoma.

BACKGROUND

Nasopharyngeal carcinoma is a malignant tumor that occurs in the top and side walls of the nasopharyngeal cavity, which is one of the most frequent malignant tumors in China with the highest incidence in otolaryngological malignant tumors. The World Health Organization (WHO) classifies nasopharyngeal carcinoma into two types: keratinizing squamous cell carcinoma and non-keratinizing carcinoma (including differentiated and undifferentiated), and the most important difference between the two types is whether there is an obvious evidence for keratinization. The former has an obvious keratinization, and is more common in the elderly and not closely related to EB virus infection. The latter accounts for the majority of nasopharyngeal carcinoma and has no obvious keratosis, and they, especially undifferentiated type, are closely related to EB virus infection. In non-keratinizing carcinoma, differentiated carcinoma cells have clear boundaries, arranged in multiple layers or pavements; while undifferentiated carcinoma cells have unclear boundaries and are in a form of syncytialization, and some are spindle-shaped. Abundant lymphocyte infiltration is commonly found in non-keratinizing carcinoma, especially undifferentiated type. In China, nasopharyngeal carcinoma is often divided into two classes: carcinoma in situ and infiltrating carcinoma. Infiltrating carcinoma includes 5 subtypes: microinvasive carcinoma, squamous cell carcinoma (with high, medium, and low differentiation), adenocarcinoma (with high, medium and low differentiation), vesicular nucleus cell carcinoma, and undifferentiated carcinoma.

Most of nasopharyngeal carcinomas are moderately sensitive to radiotherapy, and thus radiotherapy is the first choice for the treatment of nasopharyngeal carcinoma, which is disclosed in "Diagnostic Significance and Function Study of NLK Expression in Nasopharyngeal Carcinoma, Size, Chen, et al.". However, for the cases with highly differentiated carcinoma, later course of the disease and recurrence after radiotherapy, surgical resection and chemotherapy are also indispensable means. Since the complicated structure of nasopharynx and the lesions are deep and hidden, the difficulty of treatment is increased. Meanwhile, there is a lack of individualized specific treatment methods and drugs, and the therapies are relatively simplex. Therefore, the treatment effect on nasopharyngeal carcinoma is still poor, and the 5-year survival rate remains low.

SUMMARY

In an aspect, the present invention provides a method for treating nasopharyngeal carcinoma, which comprises administering a therapeutically effective amount of a compound of Formula (I) or a pharmaceutically acceptable salt thereof to a patient in need of treatment.

The chemical name of the compound of Formula (I) is 1-[[[4-(4-fluoro-2-methyl-1H-indol-5-yl)oxy-6-methoxyquinolin-7-yl]oxy]methyl]cyclopropylamine, and it has the following structural formula:

Formula (I)

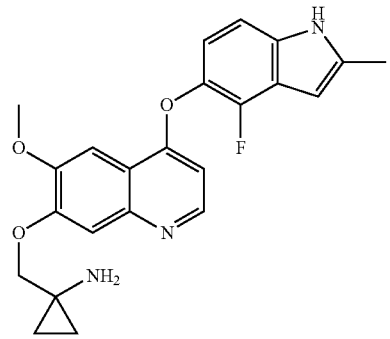

In some particular embodiments of the present invention, a method for treating keratinizing squamous cell carcinoma of the nasopharynx is provided, comprising administering a therapeutically effective amount of a compound of Formula (I) or a pharmaceutically acceptable salt thereof to a patient in need of treatment.

In some particular embodiments of the present invention, a method for treating non-keratinizing nasopharyngeal carcinoma is provided, comprising administering a therapeutically effective amount of a compound of Formula (I) or a pharmaceutically acceptable salt thereof to a patient in need of treatment, and the non-keratinizing nasopharyngeal carcinoma includes differentiated and undifferentiated type.

In some particular embodiments of the present invention, a method for treating nasopharyngeal carcinoma in situ is provided, comprising administering a therapeutically effective amount of a compound of Formula (I) or a pharmaceutically acceptable salt thereof to a patient in need of treatment.

In some particular embodiments of the present invention, a method for treating infiltrating nasopharyngeal carcinoma is provided, comprising administering a therapeutically effective amount of a compound of Formula (I) or a pharmaceutically acceptable salt thereof to a patient in need of treatment, wherein the infiltrating nasopharyngeal carcinoma includes but is not limited to squamous cell carcinoma, adenocarcinoma, microinvasive carcinoma, vesicular nucleus cell carcinoma and undifferentiated nasopharyngeal carcinoma.

In some particular embodiments of the present invention, a method for treating advanced and/or metastatic nasopharyngeal carcinoma is provided, which comprises administering a therapeutically effective amount of a compound of Formula (I) or a pharmaceutically acceptable salt thereof to a patient in need of treatment. In some particular embodiments of the present invention, the advanced and/or metastatic nasopharyngeal carcinoma metastasizes to the neck lymph, spleen and/or lung. In some particular embodiments of the present invention, the nasopharyngeal carcinoma is unresectable. In some particular embodiments of the present invention, the patient with nasopharyngeal carcinoma has previously been treated with chemotherapy drug, monoclonal antibody, and/or radiotherapy. In some preferred embodiments of the present invention, the disease progresses after the patient with nasopharyngeal carcinoma has been treated with chemotherapy, monoclonal antibody, and/or radiotherapy previously. In some more preferred embodiments of the present invention, the chemotherapy drug that the patient with nasopharyngeal carcinoma has been treated with previously includes gemcitabine, capecitabine, cisplatin, lobaplatin, nedaplatin, 5-fluorouracil, paclitaxel, docetaxel and/or cyclophosphamide; the monoclonal antibody that the patient with nasopharyngeal carcinoma has been treated with previously includes cetuximab, bevacizumab, and/or SHR-1210.

In some particular embodiments of the present invention, a method for preventing and/or treating recurrence of nasopharyngeal carcinoma is provided, comprising administering a therapeutically effective amount of a compound of Formula (I) or a pharmaceutically acceptable salt thereof to a patient in need of treatment. Compound (I) can be administered in a free base form thereof, and can also be administered in a form of a salt, hydrate and prodrug thereof (the prodrug will be converted into a free base form of Compound (I) in the body). For example, a pharmaceutically acceptable salt of Compound (I) is within the scope of the present invention, and the salt can be produced by different organic acids and inorganic acids in accordance with well-known processes in the art.

In some particular embodiments of the present invention, Compound (I) is administered in a form of hydrochloride thereof. In some particular embodiments, Compound (I) is administered in a form of monohydrochloride or dihydrochloride thereof. In some particular embodiments, Compound (I) is administered in a crystalline form of hydrochloride thereof. In some particular embodiments, Compound (I) is administered in a crystalline form of dihydrochloride thereof.

The compound of Formula (I) or a pharmaceutically acceptable salt thereof can be administered via various routes, including but not limited to: orally, parenterally, intraperitoneally, intravenously, intraarterially, transdermally, sublingually, intramuscularly, rectally, transbuccally, intranasally, via inhalation, vaginally, intraocularly, via local administration, subcutaneously, intraadiposally, intraarticularly, and intrathecally. In some particular embodiments, the administration is performed orally, and the specific formulations include tablets, capsules, dusts, granulates, drip pills, pastes, powders and the like, tablets and capsules are preferred. Among them, the tablets can be common tablets, dispersible tablets, effervescent tablets, sustained release tablets, controlled release tablets or enteric coated tablets, and the capsules can be common capsules, sustained release capsules, controlled release capsules or enteric coated capsules. The oral formulations can be prepared with well-known pharmaceutically acceptable carriers in the art by conventional methods. The pharmaceutically acceptable carriers include bulking agents, absorbing agents, wetting agents, binding agents, disintegrating agents, lubricants and the like. The bulking agents include starch, lactose, mannitol, microcrystalline cellulose and the like; the absorbing agents include calcium sulfate, calcium hydrogen phosphate, calcium carbonate and the like; the wetting agents include water, ethanol and the like; the binding agents include hydroxypropyl methylcellulose, povidone, microcrystalline cellulose and the like; the disintegrating agents include cross-linked carboxymethyl cellulose sodium, crospovidone, surfactants, low-substituted hydroxypropyl cellulose and the like; the lubricants include magnesium stearate, talc powder, polyethylene glycol, sodium dodecyl sulfate, Aerosil, talc powder and the like. The pharmaceutical excipients also include colorants, sweetening agents and the like.

In some particular embodiments of the present invention, the daily administration dosage of a compound of Formula (I) or a pharmaceutically acceptable salt thereof to the patient can be 2 mg to 20 mg; in some particular embodiments, the daily administration dosage to the patient is 5 mg to 20 mg; in some particular embodiments, the daily administration dosage to the patient is 10 mg to 16 mg; in some particular embodiments of the present invention, the daily administration dosage to the patient is 10 mg to 14 mg; in some particular embodiments, the daily administration dosage to the patient is 8 mg, 10 mg, 12 mg, 14 mg or 16 mg.

In the above treatment method, the compound of Formula (I) or a pharmaceutically acceptable salt thereof can be administered one or more times daily in a unit dose or multiple doses. In some particular embodiments of the present invention, the compound of Formula (I) or a pharmaceutically acceptable salt thereof is administered once per day.

The administration amount of the compound of Formula (I) or a pharmaceutically acceptable salt thereof can be determined according to severity of diseases, the response of diseases, any treatment-related toxicity, and age and health status of patients. Preferably, the compound of Formula (I) or the pharmaceutically acceptable salt thereof is administered in the manner of interval administration. The interval administration includes administration periods and rest periods, and during the administration periods, the compound of Formula (I) or a pharmaceutically acceptable salt thereof can be administered once or more daily. For example, the compound of Formula (I) or a pharmaceutically acceptable salt thereof is administered every day in an administration period, and then the administration is stopped for a period of time in a rest period, followed by an administration period and then a rest period, such an administration regimen can be repeated many times. Among them, the ratio of administration period to rest period in days is 2:0.5~5, preferably 2:0.5~3, more preferably 2:0.5~2, most preferably 2:0.5~1.

In some particular embodiments, the administration is continuously performed for 14 days and rest for 14 days. In some particular embodiments, the administration is continuously performed once daily for 14 days and rest for 14 days, followed by continuously administering once daily for 14 days and resting for 14 days, such an interval administration regimen with a 14-day continuous administration period and a 14-day rest period can be repeated many times.

In some particular embodiments, the administration is continuously performed for 14 days and rest for 14 days. In some particular embodiments, the administration is continuously performed once daily for 14 days and rest for 7 days, followed by continuously administering once daily for 14 days and resting for 7 days, such an interval administration regimen with a 14-day administration period and a 7-day rest period can be repeated many times.

In some particular embodiments, the administration is continuously performed for 5 days and rest for 2 days. In some particular embodiments, the administration is continuously performed once daily for 5 days and rest for 2 days, followed by continuously administering once daily for 5 days and resting for 2 days, such an interval administration regimen with a 5-day continuous administration period and a 2-day rest period can be repeated many times.

In some embodiments, the compound of Formula (I) or the pharmaceutically acceptable salt thereof is administered to the patient with nasopharyngeal carcinoma alone as the sole active ingredient. In some embodiments, the compound of Formula (I) or a pharmaceutically acceptable salt thereof is administered with another antitumor drug simultaneously or sequentially to the patient with nasopharyngeal carcinoma. In some embodiments, the another antitumor drug includes but is not limited to an alkylating agent, a platinum complex, a fluoropyrimidine derivative, camptothecin and a derivative thereof, anthraquinone antitumor antibiotic, taxane and a monoclonal antibody.

In another aspect, the present application provides a combinational pharmaceutical composition for the treatment of nasopharyngeal carcinoma, which includes (i) a compound of Formula (I) or a pharmaceutically acceptable salt thereof; and (ii) at least one second therapeutic agent.

In still another aspect, the present application provides a use of the combinational pharmaceutical composition in the preparation of a medicine for the treatment of nasopharyngeal carcinoma.

In still another aspect, the present application also provides a method for treating nasopharyngeal carcinoma, which comprises administering to a subject an effective amount of a compound of Formula (I) or a pharmaceutically acceptable salt thereof, and an effective amount of a second therapeutic agent to the subject in need thereof.

In still another aspect, the present application also provides a method for treating nasopharyngeal carcinoma, which comprises administering to a subject an effective amount of a combinational pharmaceutical composition, the combinational pharmaceutical composition includes (i) a compound of Formula (I) or a pharmaceutically acceptable salt thereof; and (ii) at least one second therapeutic agent.

In some embodiments of present application, the combinational pharmaceutical composition includes: (i) a pharmaceutical composition of a compound of Formula (I) or a pharmaceutically acceptable salt thereof and (ii) a pharmaceutical composition of at least one second therapeutic agent. In some embodiments, there is provided a combinational pharmaceutical composition for the treatment of nasopharyngeal carcinoma, comprising: (i) a compound of Formula (I) or a pharmaceutically acceptable salt thereof and (ii) at least one chemotherapy drug, and optionally combined with radiotherapy. In some embodiments, there is provided a combinational pharmaceutical composition for the treatment of nasopharyngeal carcinoma, comprising: (i) a compound of Formula (I) or a pharmaceutically acceptable salt thereof and (ii) at least one small molecular targeted anticancer drug, and optionally combined with radiotherapy. In some embodiments, a combinational pharmaceutical composition for the treatment of nasopharyngeal carcinoma is provided, which comprises: (i) a compound of Formula (I) or a pharmaceutically acceptable salt thereof; and (ii) at least one immunotherapy, and optionally combined with radiotherapy. In some embodiments, a combinational pharmaceutical composition for the treatment of nasopharyngeal carcinoma is provided, which comprises: (i) a compound of Formula (I) or a pharmaceutically acceptable salt thereof; and (ii) at least one macromolecular antibody, and optionally combined with radiotherapy.

In some embodiments, there is provided a combinational pharmaceutical composition for the treatment of nasopharyngeal carcinoma, which comprises: (i) a compound of Formula (I) or a pharmaceutically acceptable salt thereof; and (ii) platinum complex, and optionally combined with radiotherapy. In some embodiments, there is provided a combinational pharmaceutical composition for the treatment of nasopharyngeal carcinoma, which comprises: (i) a compound of Formula (I) or a pharmaceutically acceptable salt thereof; and (ii) platinum and cetuximab, and optionally combined with radiotherapy. In some embodiments, there is provided a combinational pharmaceutical composition for the treatment of nasopharyngeal carcinoma, comprising: (i) a compound of Formula (I) or a pharmaceutically acceptable salt thereof; and (ii) AK105 (Penpulimab). In some embodiments, there is provided a combinational pharmaceutical composition for the treatment of nasopharyngeal carcinoma, comprising: (i) a compound of Formula (I) or a pharmaceutically acceptable salt thereof; and (ii) AK105 (Penpulimab), and optionally combined with radiotherapy. In some embodiments, there is provided a combinational pharmaceutical composition for the treatment of nasopharyngeal carcinoma, comprising: (i) a compound of Formula (I) or a pharmaceutically acceptable salt thereof; and (ii) gemcitabine and platinum complex, and optionally combined with radiotherapy. In some embodiments, there is provided a combinational pharmaceutical composition for the treatment of nasopharyngeal carcinoma, comprising: (i) a compound of Formula (I) or a pharmaceutically acceptable salt thereof; and (ii) gemcitabine and cisplatin, and optionally combined with radiotherapy. In some embodiments, there is provided a combinational pharmaceutical composition for the treatment of nasopharyngeal carcinoma, comprising: (i) a compound of Formula (I) or a pharmaceutically acceptable salt thereof; and (ii) gemcitabine and paclitaxel, and optionally combined with radiotherapy.

In still another aspect, the present application also provides a method for treating nasopharyngeal carcinoma, which comprises administering to a subject an effective amount of the combinational pharmaceutical composition of the present application. The combinational pharmaceutical composition includes (i) a compound of Formula (I) or a pharmaceutically acceptable salt thereof; and (ii) at least one second therapeutic agent.

The method of administration can be comprehensively determined according to efficacy, toxicity, and tolerance of subject. In some embodiments of the present application, a second therapeutic agent can be administered once every day (qd), every other day (qod), every 3 days (q3d), every 4 days (q4d), every 5 days (q5d), every week (q1w), every 2 weeks (q2w), every 3 weeks (q3w), or every 4 weeks (q4w); or twice a day (bid), twice a week (biw), three times a day (tid), four times a day (qid), etc. In some embodiments of the present application, a second therapeutic agent can be administered in an interval dosing manner. The interval administration includes administration periods and rest periods. For example, a second therapeutic agent is administered every day during an administration period, and then the administration is stopped for a period of time during a rest period, followed by another administration period, and then another rest period, which can be repeated many times.

In some embodiments, a second therapeutic agent and a compound of Formula (I) or a pharmaceutically acceptable salt thereof have the same or different treatment cycles, respectively. In some specific embodiments, the second therapeutic agent and compound I or its pharmaceutically acceptable salt have the same treatment cycle, for example, every 1 week, every 2 weeks, every 3 weeks or every 4 weeks as one treatment cycle. In some specific embodiments, a second therapeutic agent and a compound of Formula (I) or its pharmaceutically acceptable salt have the same treatment cycle and every 3 weeks is one treatment cycle.

In some embodiments of the present application, a second therapeutic agent includes but is not limited to a chemotherapy drug, a small molecular targeted antitumor drug, an immunotherapy drug, or a macromolecular antibody.

In some embodiments, a chemotherapy drug includes but is not limited to one or more of platinum complex, fluoropyrimidine derivative, camptothecin and a derivative thereof, taxanes, vinblastine and a derivative thereof, anthraquinones, antibiotic antitumor drug, podophyllum-based compounds, and antimetabolite antitumor drug.

In some embodiments, examples of a chemotherapy drug include but are not limited to one or more of platinum complex (e.g., oxaliplatin, cisplatin, carboplatin, nedaplatin, dicycloplatin, lobaplatin, triplatinum tetranitrate, phenanthreneplatin, picoplatin and satraplatin), fluoropyrimidine derivatives (e.g., gemcitabine, capecitabin, ancitabine, fluorouracil, diflurouracil, deoxyfluorouridine, tegafur, carmofur, trifluorouridine), taxanes (such as paclitaxel, albumin-bound paclitaxel, and docetaxel), camptothecin and derivatives thereof (e.g., camptothecin, hydroxycamptothecin, 9-amino camptothecin, 7-ethyl camptothecin, irinotecan and topotecan), vinblastine and derivatives thereof (vinorelbine, vinblastine, vincristine, vindesine, and vinflunine), anthraquinones (such as epirubicin, adriamycin, daunorubicin, pirarubicin, amrubicin, idarubicin, mitoxantrone, aclarubicin, valrubicin, zorubicin, and pixantrone), cytarabine, thioguanine, pemetrexed, carmustine, melphalan, etoposide, teniposide, mitomycin, ifosfamide, cyclophosphamide, azacitidine, methotrexate, bendamustine, liposome adriamycin, actinomycin D, bleomycin, bleomycin A5, temozolomide, decarbazine, peplomycin, eribulin, plinabulin, sapacitabine, treosulfan, 153Sm-EDTMP, the S-1 regimen and encequidar.

In some particular embodiments, a second therapeutic agent is selected from the group consisting of one or more of platinum complex, wherein the platinum complex includes but is not limited to cisplatin, carboplatin, nedaplatin, oxaliplatin, triplatinum tetranitrate, phenanthreneplatin, picoplatin, satraplatin, and lobaplatin.

If necessary, a second therapeutic agent is used in conjunction with chemotherapy adjuvant drugs. The chemotherapy adjuvant drugs include, but not limited to, calcium folinate (CF), leucovorin, mesna, bisphosphonates, amifostine, and hematopoietic colony stimulating factors (CSFs). In some embodiments, the chemotherapy adjuvant drug is calcium folinate (CF), mesna, or leucovorin.

In some embodiments, a second therapeutic agent is an immunotherapy drug, including but not limited to one or more of interferon (interferon α, interferon α-1b, interferon α-2b), interleukin, sirolimus, everolimus, ridaforolimus, and temsirolimus.

In some embodiments, a second therapeutic agent is a small molecular targeted antitumor drug, including but not limited to protein kinase inhibitors. Among them, the protein kinase inhibitors include but are not limited to tyrosine kinase inhibitors, serine and/or threonine kinase inhibitors, and poly ADP-ribose polymerase inhibitors. The targets of the inhibitors include but are not limited to Fascin-1protein, HDAC (histone deacetylase), Proteasome, CD38, SLAMF7 (CS1/CD319/CRACC), Proteasome, RANKL, EGFR (epidermal growth factor receptor), anaplastic lymphoma (ALK), MET gene, ROS1 gene, HER2 gene, RET gene, BRAF gene, PI3K signaling pathway, DDR2 (discoidin domain receptor 2) gene, FGFR1 (fibroblast growth factor receptor 1), NTRK1 (neurotrophic tyrosine kinase type 1 receptor) gene, and KRAS gene. The targets of the small molecule targeting antitumor drugs also include COX-2 (epoxidase-2), APE1 (apurinic-apyrimidinic endonuclease I), VEGFR-2 (vascular endothelial growth factor receptor-2), CXCR-4 (chemokine receptor-4), MMP (matrix metalloproteinase), IGF-1R (insulin-like growth factor receptor), Ezrin, PEDF (pigmented epithelial derived factor), AS, ES, OPG (bone protective factor), Src, IFN, ALCAM (activated leukocyte cell adhesion molecule), HSP, JIP1, GSK-3β (Glycogen Synthetic Kinase 3β), CyclinD1 (Cell cycle regulator protein), CDK4 (cyclin-dependent kinase), TIMP1 (tissue metalloproteinase inhibitor), THBS3, PTHR1 (parathyroid hormone-related protein receptor 1), TEM7 (human tumor vascular endothelial marker 7), COPS3, and cathepsin K. Examples of small-molecule targeted anti-tumor drugs include but are not limited to one or more of imatinib, sunitinib, nilotinib, bosutinib, saracatinib, pazopanib, trabectedin, regorafenib, cediranib, bortezomib, panobinostat, carfilzomib, ixazomib, apatinib, erlotinib, afatinib, crizotinib, ceritinib, vemurafenib, dabrafenib, cabozantinib, gefitinib, dacomitinib, osimertinib, alectinib, brigatinib, lorlatinib, trametinib, larotrectinib, icotinib, lapatinib, vandetanib, selumetinib, sorafenib, olmutinib, savolitinib, fruquintinib, entrectinib, dasatinib, ensartinib, lenvatinib, itacitinib, pyrotinib, binimetinib, erdafitinib, axitinib, neratinib, cobimetinib, acalabrutinib, famitinib, masitinib, ibrutinib, rociletinib, nintedanib, lenalidomide, LOXO-292, vorolanib, bemcentinib, capmatinib, entrectinib, TAK-931, ALT-803, palbociclib, famitinib L-malate, LTT-462, BLU-667, ningetinib, tipifarnib, poziotinib, DS-1205c, capivasertib, SH-1028, metformin, seliciclib, OSE-2101, APL-101, berzosertib, idelalisib, lerociclib, ceralasertib, PLB-1003, tomivosertib, AST-2818, SKLB-1028, D-0316, LY-3023414, allitinib, MRTX-849, AP-32788, AZD-4205, lifirafenib, vactosertib, mivebresib, napabucasin, sitravatinib, TAS-114, molibresib, CC-223, rivoceranib, CK-101, LXH-254, simotinib, GSK-3368715, TAS-0728, masitinib, tepotinib, HS-10296, AZD-4547, melestinib, olaptesed pegol, galunisertib, ASN-003, gedatolisib, defactinib, lazertinib, CKI-27, S-49076, BPI-9016M, RF-A-089, RMC-4630, AZD-3759, antroquinonol, SAF-189s, AT-101, TTI-101, naputinib, LNP-3794, HH-SCC-244, ASK-120067, CT-707, epitinib succinate, tesevatinib, SPH-1188-11, BPI-15000, copanlisib, niraparib, olaparib, veliparib, talazoparib tosylate, DV-281, Siremadlin, Telaglenastat, MP-0250, GLG-801, ABTL-0812, bortezomib, tucidinostat, vorinostat, resminostat, epacadostat, tazemetostat, entinostat, mocetinostat, quisinostat, LCL-161, and KML-001. In some embodiments, the small-molecule targeted anti-tumor drug is selected from the group consisting of one or more of sorafenib, erlotinib, afatinib, crizotinib, ceritinib, vemurafenib, dabrafenib, cabozantinib, gefitinib, dacomitinib, osimertinib, alectinib, brigatinib, lorlatinib, trametinib, larotrectinib, icotinib, lapatinib, vandetanib, selumetinib, olmutinib, savolitinib, fruquintinib, entrectinib, dasatinib, ensartinib, lenvatinib, itacitinib, pyrotinib, binimetinib, erdafitinib, axitinib, neratinib, cobimetinib, acalabrutinib, famitinib, masitinib, ibrutinib, and nintedanib.

In some embodiments, a second therapeutic agent is macromolecular antibody. Among them, the targets of a macromolecular antibody include but are not limited to one or more of PD-1, PD-L1, cytotoxic T-lymphocyte antigen 4 (CTLA-4), platelet-derived growth factor receptor α

(PDGFR-α), vascular endothelial growth factor (VEGF), human epidermal growth factor receptor-2 (HER2), epidermal growth factor receptor (EGFR), ganglioside GD2, B cell surface protein CD20, B cell surface protein CD52, B cell surface protein CD38, B cell surface protein CD319, B cell surface protein CD30, and B cell surface protein CD19/CD3.

In some embodiments, the antibody is an inhibitor of the interaction between the PD-1 receptor and its ligand PD-L1. In some embodiments, the antibody is a cytotoxic T-lymphocyte antigen 4 (CTLA-4) inhibitor. In some embodiments, the antibody is a platelet-derived growth factor receptor alpha (PDGFR-α) inhibitor. In some embodiments, the inhibitor of the interaction between the PD-1 receptor and its ligand PD-L1 is an antibody or the antigen-binding portion that binds to programmed death receptor 1 (PD-1) and/or inhibits the PD-1 activity, alternatively, an antibody or antigen-binding portion that binds to PD-L1 and/or inhibits PD-L1 activity, for example, an anti-PD-1 antibody or an anti-PD-L1 antibody. In some specific embodiments, the antibody or antigen-binding portion thereof is (a) a monoclonal antibody, or an antigen-binding fragment thereof, which specifically binds human PD-1 and blocks the binding of human PD-L1 to human PD-1; or (b) a monoclonal antibody, or an antigen-binding fragment thereof, that specifically binds human PD-L1 and blocks the binding of human PD-L1 to human PD-1.

In some embodiments, the anti-PD-1 or PD-L1 antibody is an anti-PD-1 or an anti-PD-L1 monoclonal antibody.

In some embodiments, the anti-PD-1 or PD-L1 antibody is a human antibody or a murine antibody.

In some embodiments, the anti-PD-1 antibody can be selected from the group consisting of one or more of nivolumab, pembrolizumab, durvalumab, and toripalimab (JS-001), centilimab (IBI308), carrelizumab, tirelizumab (BGB-A317), AK105 (Akeso, Inc.), genolimzumab (GB226), livuzumab (LZM009), HLX-10, BAT-1306, AK103 (HX008), AK104 (Akeso, Inc.), CS1003, SCT-I10A, F520, SG001, and GLS-010.

In some embodiments, the anti-PD-L1 antibody can be selected from the group consisting of one or more of atezolizumab, avelumab, durvalumab, KL-A167, SHR-1316, BGB-333, JS003, STI-A1014 (ZKAB0011), KN035, MSB2311, HLX-20, and CS-1001.

In some specific embodiments, the anti-PD-1 antibody is toripalimab.

In some specific embodiments, the anti-PD-1 antibody is pembrolizumab.

In some specific embodiments, the anti-PD-1 antibody is AK105.

In some embodiments, the cytotoxic T-lymphocyte antigen 4 (CTLA-4) inhibitor is an anti-CTLA-4 antibody. In some specific embodiments, the anti-CTLA-4 antibody is an anti-CTLA-4 monoclonal antibody.

In some embodiments, the anti-CTLA-4 antibody can be selected from the group consisting of one or more of ipilimumab, tremelimumab, AGEN-1884, BMS-986249, BMS-986218, AK-104, and IBI310.

In some specific embodiments, the anti-CTLA-4 antibody is ipilimumab.

In some embodiments, the platelet-derived growth factor receptor alpha (PDGFR-α) inhibitor is an anti-PDGFRα antibody. In some specific embodiments, the anti-PDGFRα antibody is an anti-PDGFRα monoclonal antibody.

In some specific embodiments, the anti-PDGFRα antibody is olaratumab.

In some specific embodiments, the antibody drug can also include but is not limited to one or more of bevacizumab, ramucirumab, pertuzumab, trastuzumab, cetuximab, nimotuzumab, panitumumab, necitumumab, dinutuximab, rituximab, ibritumomab, ofatumumab, obinutuzumab, alemtuzumab, daratumumab, gemtuzumab, elotuzumab, brentuximab, inotuzumab ozogamicin, and blinatumomab.

In some embodiments, a second therapeutic agent can be selected from the group consisting of one or more of methotrexate, cisplatin, carboplatin, paclitaxel, docetaxel, fluorouracil, vinorelbine, bleomycin, ifosfamide, mesna, leucovorin, mitoxantrone, pirarubicin, daunorubicin, cytarabine, thioguanine, etoposide, harringtonine, gemcitabine, cetuximab, and epirubicin. In some embodiments, the second therapeutic agent is at least one selected from the group consisting of: (1) methotrexate, TS-1 or paclitaxel; (2) platinum complex and 5-fluorouracil; (3) platinum complex and cetuximab; (4) gemcitabine and vinorelbine; (5) gemcitabine and paclitaxel; (6) paclitaxel and carboplatin; (7) daunorubicin and cytarabine; (8) mitoxantrone and etoposide; (9) gemcitabine and cisplatin; (10) adriamycin and cisplatin; (11) ifosfamide, mesna, and etoposide; (12) docetaxel, cisplatin, and 5-fluorouracil; (13) cisplatin, epirubicin, and paclitaxel; (14) platinum complex, 5-fluorouracil, and cetuximab; (15) platinum complex, docetaxel, and paclitaxel; (16) arboplatin, paclitaxel, and gemcitabine; (17) vinorelbine, methotrexate, and bleomycin; (18) vinorelbine, methotrexate, and bleomycin; (19) cisplatin, bleomycin, and fluorouracil; (20) cisplatin, bleomycin, and fluorouracil; (21) mitoxantrone, fluorouracil, and carboplatin; (22) adriamycin, cisplatin, and fluorouracil; (23) daunorubicin, cytarabine, thioguanine, and etoposide; (24) harringtonine, cytarabine, and thioguanine; and (25) harringtonine, vincristine, cytarabine, and prednisone.

In some embodiments, a second therapeutic agent is methotrexate, specifically methotrexate 40 mg/m$^2$ is administed IV on the first day, once every 7 days.

In some embodiments, a second therapeutic agent is paclitaxel, specifically paclitaxel 250 mg/m$^2$ is administed CIV on the first day, repeated every 21 days.

In some embodiments, a second therapeutic agent is at least one selected from the group consisting of carboplatin and 5-fluorouracil.

In some embodiments, a second therapeutic agent is at least one selected from the group consisting of cisplatin and cetuximab.

In some embodiments, a second therapeutic agent is at least one selected from the group consisting of carboplatin and cetuximab.

In some embodiments, a second therapeutic agent is at least one selected from the group consisting of gemcitabine and vinorelbine.

In some embodiments, a second therapeutic agent is at least one selected from the group consisting of gemcitabine and paclitaxel.

In some embodiments, a second therapeutic agent is at least one selected from the group consisting of cisplatin and fluorouracil, specifically the DF regimen.

In some embodiments, the second therapeutic agent is at least one selected from the group consisting of paclitaxel and carboplatin, specifically the PC regimen.

In some embodiments, the second therapeutic agent is at least one selected from the group consisting of daunorubicin and cytarabine, specifically the DA regimen.

In some embodiments, the second therapeutic agent is at least one selected from the group consisting of mitoxantrone and etoposide, specifically the ME regimen.

In some embodiments, the second therapeutic agent is at least one selected from the group consisting of gemcitabine and cisplatin, specifically the GP regimen.

In some embodiments, the second therapeutic agent is at least one selected from the group consisting of 5-fluorouracil and cisplatin, specifically the FP regimen.

In some embodiments, the second therapeutic agent is at least one selected from the group consisting of adriamycin and cisplatin, specifically the AP regimen.

In some embodiments, the second therapeutic agent is at least one selected from the group consisting of ifosfamide, mesna, and etoposide, specifically the IE regimen.

In some embodiments, the second therapeutic agent is at least one selected from the group consisting of docetaxel, cisplatin, and 5-fluorouracil.

In some embodiments, the second therapeutic agent is at least one selected from the group consisting of cisplatin, epirubicin, and paclitaxel.

In some embodiments, the second therapeutic agent is at least one selected from the group consisting of cisplatin, 5-fluorouracil, and cetuximab.

In some embodiments, the second therapeutic agent is at least one selected from the group consisting of carboplatin, 5-fluorouracil, and cetuximab.

In some embodiments, the second therapeutic agent is at least one selected from the group consisting of cisplatin, docetaxel, and paclitaxel.

In some embodiments, the second therapeutic agent is at least one selected from the group consisting of carboplatin, docetaxel, and paclitaxel.

In some embodiments, the second therapeutic agent is at least one selected from the group consisting of carboplatin, paclitaxel, and gemcitabine.

In some embodiments, the second therapeutic agent is at least one selected from the group consisting of vinorelbine, methotrexate, and bleomycin, specifically the NMB regimen.

In some embodiments, the second therapeutic agent is at least one selected from the group consisting of paclitaxel, ifosfamide, mesna and cisplatin, specifically the PIC regimen.

In some embodiments, the second therapeutic agent is at least one selected from the group consisting of cisplatin, fluorouracil, and leucovorin, specifically the DLF regimen.

In some embodiments, the second therapeutic agent is at least one selected from the group consisting of cisplatin, bleomycin, and fluorouracil, specifically the PBF regimen.

In some embodiments, the second therapeutic agent is at least one selected from the group consisting of mitoxantrone, fluorouracil, and carboplatin, specifically the MFC regimen.

In some embodiments, the second therapeutic agent is at least one selected from the group consisting of adriamycin, cisplatin, and fluorouracil, specifically the TPF regimen.

In some embodiments, the second therapeutic agent is at least one selected from the group consisting ofo daunorubicin, cytarabine, thioguanine, and etoposide, specifically the DAT regimen.

In some embodiments, the second therapeutic agent is at least one selected from the group consisting of harringtonine, cytarabine, and thioguanine, specifically the HA regimen.

In some embodiments, the second therapeutic agent is at least one selected from the group consisting of harringtonine, vincristine, cytarabine, and prednisone, specifically the HOAP regimen.

In some embodiments, the second therapeutic agent is the S-1 regimen.

In another aspect, the present invention provides use of the compound of Formula (I) or the pharmaceutically acceptable salt thereof in manufacturing a pharmaceutical composition for treating nasopharyngeal carcinoma.

In still another aspect, the present invention provides a pharmaceutical composition for treating nasopharyngeal carcinoma comprising a compound of Formula (I) or a pharmaceutically acceptable salt thereof, and at least one pharmaceutically acceptable carrier.

In yet another aspect, the present invention provides a kit, comprising (a) at least one unit dose of a pharmaceutical composition of a compound of Formula (I) or a pharmaceutically acceptable salt thereof, and (b) instructions for treatment of nasopharyngeal carcinoma.

Unless indicated otherwise, for the purpose of the present application, the following terms used in the Description and Claims are intended to have the meanings denoted below. A "patient" refers to mammal, preferably human.

"Pharmaceutically acceptable" means those which are useful in preparing a pharmaceutical composition that is generally safe, non-toxic and neither biologically nor otherwise undesirable, and that is acceptable for human pharmaceutical use when the carriers are included.

"Pharmaceutically acceptable salt" includes, but not limited to acid addition salt formed from inorganic acid, such as hydrochloric acid, hydrobromic acid, sulfuric acid, nitric acid, phosphoric acid and the like; or acid addition salt formed from organic acid, such as acetic acid, trifluoroacetic acid, propionic acid, caproic acid, heptanoic acid, cyclopentane propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methyl sulfonic acid, ethyl sulfonic acid, 1,2-ethanedisulfonic acid, 2-hydroxyethanesulphonic acid, benzenesulfonic acid, p-chlorobenzenesulfonic acid, p-toluenesulfonic acid, 3-phenylpropionic acid, trimethylacetic acid, t-butylacetic acid, dodecyl sulfuric acid, gluconic acid, glutamic acid, hydroxynaphthoic acid, salicylic acid, stearic acid and the like.

"Therapeutically effective amount" means an amount of a compound that, when administered to human for treating a disease, is sufficient to achieve control of the disease. For example, the term "therapeutically effective amount" as used herein refers to the amount or quantity of a drug or pharmaceutically active substance which is sufficient to elicit the required or desired therapeutic response, or in other words, the amount which is sufficient to elicit an appreciable biological response when administered to a patient.

"Subject" and "patient" can be used interchangeably, and referring to a mammal, preferably, referring to a human.

"Treatment/treating" means any administration of a therapeutically effective amount of a compound, and includes:

(1) Inhibiting or reducing the symptoms of a disease in human body that is experiencing or displaying the pathology or symptomatology of the disease (i.e., retarding further progression of the pathology and/or symptomatology), or (2) Ameliorating a disease in human body that is experiencing or displaying the pathology or symptomatology of the disease (i.e., reversing the pathology and/or symptomatology).

"CR" refers to complete remission, which means that target lesions of tumors have disappeared and no new lesions appear which is maintained for at least 4 weeks.

"PR" refers to partial remission, which means 30% or more decrease in the sum of the diameters of target lesions of tumors than the baseline level, which is maintained for at least 4 weeks.

"PD" refers to the progression of disease, which means 20% or more increase in the diameters of target lesions of tumors than the baseline level.

"SD" refers to stable disease, which means the sum of diameters of all target leisions neither shrink to qualify for PR nor sufficient increase to qulify for PD.

"qd" refers to taking the drug once per day.

"Advanced" includes "locally advanced".

"Gy" refers to the gray, a derived unit of ionizing radiation dose. It is defined as the absorption of one joule of radiation energy per kilogram of matter.

DETAILED EMBODIMENTS OF THE INVENTION

EXAMPLE 1

1-[[[4-fluoro-2-methyl-1H-indol-5-yl)oxy-6-methoxyquinolin-7-yl]oxy]methyl]cyclopropylamine dihydrochloride

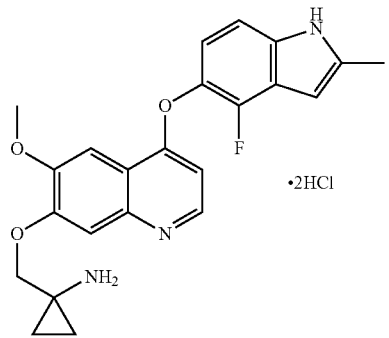 [SMILES: COc1cc2c(Oc3ccc4[nH]c(C)cc4c3F)ccnc2cc1OCC1(N)CC1 ; "·2HCl"]

1-[[[4-fluoro-2-methyl-1H-indol-5-yl)oxy-6-methoxy-quinolin-7-yl]oxy]methyl]cyclopropylamine was prepared by reference to the method of Example 24 in WO2008112407, and then the title compound was prepared by reference to the preparation method in "Examples of Salt Formation" of the Description of WO2008112407.

EXAMPLE 2

Preparation of Capsules of 1-[[[4-fluoro-2-methyl-1H-indol-5-yl)oxy-6-methoxyquinolin-7-yl]oxy]methyl]cyclopropylamine dihydrochloride (Compound of Example 1)

| active ingredient/excipient | amount (1000 capsules) |
| --- | --- |
| The compound of Example 1 | 14.16 g |
| Mannitol | 89 g |
| Microcrystalline cellulose | 138.4 g |
| Hydroxypropyl cellulose | 5.9 g |
| Magnesium stearate | 0.99 g |

The compound of Example 1 was grinded and sifted with a 80 mesh sieve, and then mixed uniformly with mannitol and hydroxypropyl cellulose; the prescribed amount of microcrystalline cellulose was subsequently added, mixed uniformly and sifted with a 0.8 mm sieve; and finally, the prescribed amount of magnesium stearate was added and mixed uniformly, and the obtained mixture was filled into capsules.

The capsule in which dihydrochloride of Compound I is at different content can be prepared by reference to the above proportion and formulation.

EXAMPLE 3

Screening of Enrolled Patients:
1) Having been definitely diagnosed with nasopharyngeal carcinoma based on pathology or cytology;
2) With measurable lesions (according to RECIST 1.1);
3) Lack of effective conventional treatment, or conventional treatment failure or relapse;
4) The body mass index (BMI) meets: 20≤BMI≤25;
5) 18≤age≤70; ECOG score: 0 to 1; expected survival time: more than 3 months;
6) The function of the main organs is normal;
7) Women should agree to take contraceptive measures (e.g. intrauterine device [IUD], condom) during the study period and within 6 months after the end of the study period, should be negative for serum or urine pregnancy test within 7 days before enrolled to the study, and must be non-lactating subjects; and men should agree to take contraceptive measures during the study period and within 6 months after the end of the study period;
8) The patients voluntarily join the study, sign an informed consent form, and have good compliance.

Treatment Regimen:
During or after radiotherapy, the patients are treated with the capsules of the compound of Example 1 at 12 mg qd. The administration is continuously performed for 2 weeks and rest for 1 week, followed by continuously administrating for 2 weeks and resting for 1 week as a cycle. The target lesions are regularly evaluated, and the treatment regimen is terminated according to the evaluation results.

EXAMPLE 4

Efficacy on Nasopharyngeal Carcinoma

A 53-year-old male patient was diagnosed with nasopharyngeal non-keratinizing undifferentiated carcinoma by nasopharyngoscopy biopsy on Nov. 19, 2014. On Nov. 29, 2014, MRI on nasopharynx indicated multiple swollen lymph nodes in the bilateral jaws and lower neck.

From Dec. 16, 2014 to Jan. 26, 2015, paclitaxel, cisplatin and 5-fluorouracil were administered, the induction chemotherapy was performed for 3 cycles, and the chemotherapy was successful. From Feb. 25, 2015 to April 2015, 68 Gy was given to the nasopharynx and 70 Gy to the left and right neck lymph nodes for radiotherapy, with a total of 30 times; and treatment of cetuximab and cisplatin was performed at the same period. Subsequent periodic examinations showed the disease was stable.

On Nov. 20, 2015, PET/CT showed spleen metastasis after nasopharyngeal carcinoma radiotherapy, indicating progression of the disease. Based on the EBV-DNA results on Jan. 8, 2016, it was considered a recurrence of nasopharyngeal carcinoma. From Jan. 27, 2016 to May 27, 2016, the patient was enrolled in the ML29153 clinical trial with informed consent, and treated with docetaxel, cyclophosphamide and bevacizumab for 6 cycles, the treatment was completed successfully. Adverse reactions such as bone marrow suppression occurred during the treatment, which was relieved after symptomatic treatment.

From June 2016 to July 2017, bevacizumab was given for 14 cycles, and the tumors were stable which was determined by examination during the administration. Afterwards, examination was conducted again, which indicated that multiple lymph nodes appeared adjacent the abdominal aorta, evaluated as PD.

Subsequently, the patient took orally the capsules of 12 mg of the compound of Example 1 once per day for treatment (continuously administrating for 2 weeks and resting for 1 week as a treatment cycle). After 2 cycles of the treatment, the enhanced CT showed that the left anterior lymph nodes of the abdominal aorta and the right anterior lymph nodes of the abdominal aorta were slightly smaller than before, evaluated as PR according to RECIST 1.1; and the sum of the target lesions was 12 mm, which was reduced by 7 mm from the baseline. After 4 cycles of treatment, evaluated as PR according to RECIST 1.1, and the sum of the target lesions was 10 mm, which was reduced by 9 mm from the baseline. After 8 cycles of treatment, the sum of the target lesions was 9 mm, which was reduced by 10 mm from the baseline.

Grade 3 hypertension occurred during the administration of the capsules of the compound of Example 1, and the symptoms of hypertension were relieved after medication and dosage reduction.

EXAMPLE 5

Efficacy on Nasopharyngeal Carcinoma

A 58-year-old female patient was suspected of nasopharyngeal carcinoma by PET-CT in February 2012, and was diagnosed as non-keratinizing undifferentiated carcinoma by biopsy pathology. CT showed metastasis in the right retropharyngeal lymph nodes, the lymph nodes in level II of the right neck and the nodules in the right middle lung.

Treatment of Gemcitabine and cisplatin was given from Apr. 18, 2012 to Aug. 22, 2012 for 6 cycles, and the best overall response was PR. On Apr. 21, 2016, CT showed enlarged lung masses and axillary lymph nodes after examination, indicating disease progression.

From Jun. 16, 2016 to Oct. 18, 2016, treatment of docetaxel and cyclophosphamide was given for 6 cycles, and the best overall response was PR. Grade 3 leukopenia, Grade 2 platelet decrease and symptoms of low fever occurred during treatment, which was alleviated after appropriate treatment. When examination was conducted again on Feb. 10, 2017, CT results indicated disease progression.

From Mar. 2, 2017, the patient started to take orally the capsules of 12 mg of the compound of Example 1 once per day for treatment (continuously administrating for 2 weeks and resting for 1 week as a treatment cycle). On Apr. 12, 2017, after 2 cycles of treatment, the enhanced CT showed that the nodules in the middle lobe of the right lung were smaller than before, evaluated as PR according to RECIST 1.1; and the sum of the target lesions was 30 mm, which was reduced by 17 mm from the baseline. The treatment with the capsules of the compound of Example 1 was continued.

On May 22, 2017, after 4 cycles of the chemotherapy, the enhanced CT showed that the nodules in the middle lobe of the right lung was slightly smaller than before, evaluated as PR according to RECIST 1.1; and the sum of the target lesions was 28 mm, which was reduced by 19 mm from the baseline. The treatment with the capsules of the compound of Example 1 was continued. On Jul. 3, 2017, after 6 cycles of the treatment, the enhanced CT showed that the nodules in the middle lobe of the right lung was slightly smaller than before, evaluated as PR according to RECIST 1.1; and the sum of the target lesions was 24 mm, which was reduced by 23 mm from the baseline. The treatment with the capsules of the compound of Example 1 was continued. From Aug. 14, 2017 to Nov. 6, 2017, after 12 cycles of the treatment, the enhanced CT showed no change in the nodules in the middle lobe of the right lung, evaluated as PR according to RECIST 1.1; and the results of the efficacy evaluation showed that the sum of the target lesions was 24 mm, which was reduced by 23 mm from the baseline. On Jan. 29, 2018, after 16 cycles of the treatment, the enhanced CT showed no change in the nodules in the middle lobe of the right lung, evaluated as PR according to RECIST 1.1; and the results of the efficacy evaluation showed that the sum of the target lesions was 23 mm, which was reduced by 24 mm from the baseline.

EXAMPLE 6

Efficacy on Nasopharyngeal Carcinoma

A 44-year-old male patient was diagnosed with nasopharyngeal non-keratinizing undifferentiated carcinoma by nasopharyngoscopy biopsy. MRI on the nasopharynx and neck indicated multiple swollen lymph nodes and metastasis in the right carotid artery sheath and deep neck.

Subsequently, a combined chemotherapy of docetaxel, cisplatin and capecitabine was administered for 3 cycles, and the best overall response was PR, with mild adverse reactions during this period. IMRT precise radiotherapy was performed 1 month after the end of the chemotherapy, with the doses of GTV 70Gy/33f, GTVnd(R/L) 66Gy/33f, and CTV 62Gy/33f; and cisplatin was administered at the same period. The disease was stable after two cycles of treatment and then periodic examination was performed.

The examination was conducted again afterwards, and CT showed multiple nodules dispersing in both lungs, indicating the progression of the disease. The pathological results of the lung masses by puncture biopsy confirmed the diagnosis of Stage IV of pulmonary metastasis after radiotherapy and chemotherapy of nasopharyngeal non-keratinizing undifferentiated carcinoma. A combined chemotherapy of Gemcitabine, cisplatin and SHR-1210 was given for 6 cycles, and the best overall response was PR, with occurrence of Grade 2 leukopenia after treatment and then alleviated after treatment of increasing leucocyte. A combined chemotherapy of Gemcitabine, cisplatin and SHR-1210 was then given for 8 cycles, and the best overall response reached PR, and afterwards evaluated as the progression of the disease (PD).

Three months later, the patient started to take orally the capsules of 12 mg of the compound of Example 1 once per day for treatment (continuously administrating for 2 weeks and resting for 1 week as a treatment cycle). After 2 cycles of the treatment, the enhanced CT showed that the lymph nodes next to the right lower bronchus, the nodules in the right lower lung, and the nodules in the right adrenal gland were slightly smaller than before, evaluated as SD according to RECIST 1.1; and the sum of the target lesions was 47 mm, which was reduced by 18 mm from the baseline. The treatment with the capsules of the compound of Example 1 was continued. After 4 cycles of the treatment, the enhanced CT showed that the lymph nodes next to the right lower bronchus, the nodules in the right lower lung, and the nodules in the right adrenal gland were slightly smaller than before, evaluated as PR according to RECIST 1.1; and the sum of the target lesions was 42 mm, which was reduced by 23 mm from the baseline.

Grades 2 and 3 hypertension occurred successively during the administration of the capsules of the compound of Example 1, and then alleviated by administration of antihypertensive drugs and dose reduction to 10 mg and 8 mg successively during the treatment.

What is claimed is:

1. A method for treating advanced and/or metastatic and/or recurrent nasopharyngeal carcinoma in a subject, the method comprising administering a therapeutically effective amount of a compound of Formula (I) or a pharmaceutically acceptable salt thereof to the subject in need thereof,

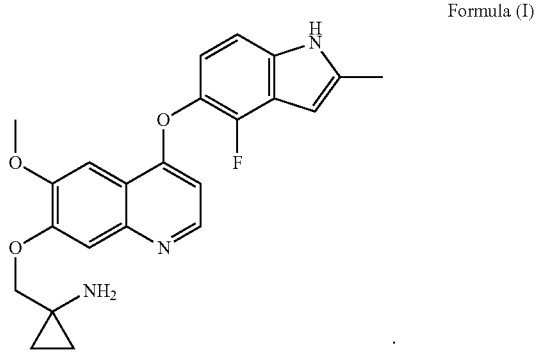 [SMILES: COc1cc2c(Oc3ccc4[nH]c(C)cc4c3F)ccnc2cc1OCC1(N)CC1]

Formula (I)

2. The method of claim 1, wherein the nasopharyngeal carcinoma is keratinizing squamous cell carcinoma or non-keratinizing nasopharyngeal carcinoma.

3. The method of claim 2, wherein the non-keratinizing nasopharyngeal carcinoma is differentiated or undifferentiated type.

4. The method of claim 1, wherein the nasopharyngeal carcinoma is nasopharyngeal carcinoma in situ or infiltrating nasopharyngeal carcinoma.

5. The method of claim 4, wherein the infiltrating nasopharyngeal carcinoma is squamous cell carcinoma, adenocarcinoma, microinvasive carcinoma, vesicular nucleus cell carcinoma, or undifferentiated nasopharyngeal carcinoma.

6. The method of claim 1, wherein the nasopharyngeal carcinoma is advanced and/or metastatic nasopharyngeal carcinoma.

7. The method of claim 6, wherein the subject has been treated with chemotherapy drug, monoclonal antibody, and/or radiotherapy.

8. The method of claim 1, wherein the pharmaceutically acceptable salt of the compound of Formula (I) is a salt formed by the compound of Formula (I) with an acid selected from the group consisting of hydrochloric acid, hydrobromic acid, sulfuric acid, nitric acid, phosphoric acid, acetic acid, trifluoroacetic acid, propionic acid, caproic acid, heptanoic acid, cyclopentane propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methyl sulfonic acid, ethyl sulfonic acid, 1,2-ethanedisulfonic acid, 2-hydroxyethanesulphonic acid, benzenesulfonic acid, p-chlorobenzenesulfonic acid, p-toluenesulfonic acid, 3-phenyl-propionic acid, trimethylacetic acid, t-butylacetic acid, dodecyl sulfuric acid, gluconic acid, glutamic acid, hydroxynaphthoic acid, salicylic acid, and stearic acid.

9. The method of claim 8, wherein the pharmaceutically acceptable salt of the compound of Formula (I) is a hydrochloride salt.

10. The method of claim 1, wherein the daily dose of the compound of Formula (I) or the pharmaceutically acceptable salt administered is selected from the group consisting of 2 mg to 20 mg, 5 mg to 20 mg, 10 mg to 16 mg, 10 mg to 14 mg, 8 mg, 10 mg, 12 mg, 14 mg, and 16 mg.

11. The method of claim 1, wherein the compound of Formula (I) or a pharmaceutically acceptable salt thereof is administered by an interval administration regimen including administration periods and rest periods, and the ratio of the administration period to the rest period in days is 2:0.5-5, 2:0.5~3, 2:0.5~2, or 2:0.5~1.

12. The method of claim 1, wherein a compound of Formula (I) or the pharmaceutically acceptable salt thereof is administered by an interval administration regimen with a 14-day administration period and followed by a 7-day rest period.

13. The method of claim 1, which further comprises administering to the subject another antitumor drug simultaneously or sequentially.

14. The method of claim 13, wherein the another antitumor drug is selected from the group consisting of an alkylating agent, a platinum complex, a fluoropyrimidine derivative, camptothecin and a derivative thereof, anthraquinone antitumor antibiotic, taxane, and a monoclonal antibody.

15. A method for treating advanced and/or metastatic and/or recurrent nasopharyngeal carcinoma in a subject, the method comprising administering to the subject in need thereof an effective amount of a combined pharmaceutical composition comprising (i) a compound of Formula (I) or a pharmaceutically acceptable salt thereof; and (ii) at least one second therapeutic agent,

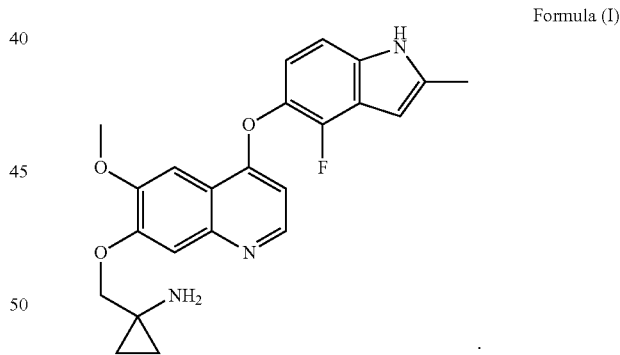

Formula (I)

16. The method of claim 15, wherein the combined pharmaceutical composition comprises:
    (i) a pharmaceutical composition comprising a compound of Formula (I) or a pharmaceutically acceptable salt thereof and (ii) a pharmaceutical composition comprising at least one second therapeutic agent.

17. The method of claim 15, wherein the second therapeutic agent is a chemotherapy drug, a small molecular targeted antitumor drug, an immunotherapy drug, or a macromolecular antibody.

18. The method of claim 17, wherein the chemotherapy drug is selected from the group consisting of a platinum complex, fluoropyrimidine derivative, camptothecin and a derivative thereof, taxane, vinblastine and a derivative thereof, anthraquinone, antibiotic antitumor drug, podophyllum-based compound, antimetabolite antitumor drug, and a combination thereof.

19. The method of claim 17, wherein the macromolecular antibody is selected from the group consisting of nivolumab, pembrolizumab, durvalumab, and toripalimab, centilimab, carrelizumab, tirelizumab, AK105, genolimzumab, livuzumab, HLX-10, BAT-1306, AK103, AK104, CS1003, SCT-I10A, F520, SG001, and GLS-010, and a combination thereof.

20. The method of claim 15, wherein the combined pharmaceutical composition comprises one of the following:
  (a) the compound of Formula (I) or pharmaceutically acceptable salt thereof, a platinum complex, and optionally combined with radiotherapy;
  (b) the compound of Formula (I) or pharmaceutically acceptable salt thereof, a platinum complex, and Cetuximab, and optionally combined with radiotherapy;
  (c) the compound of Formula (I) or pharmaceutically acceptable salt thereof, a platinum complex, and gemcitabine, and optionally combined with radiotherapy; and
  (d) the compound of Formula (I) or pharmaceutically acceptable salt thereof, gemcitabine, paclitaxel, and optionally combined with radiotherapy.

21. The method of claim 1, wherein the method for treating recurrent nasopharyngeal carcinoma.

22. The method of claim 15, wherein the method for treating recurrent nasopharyngeal carcinoma.

\* \* \* \* \*